US006242239B1

(12) United States Patent
Gröner et al.

(10) Patent No.: US 6,242,239 B1
(45) Date of Patent: Jun. 5, 2001

(54) PROCESS FOR SEPARATING HIV FROM A FLUID

(75) Inventors: Albrecht Gröner, Seeheim; Jürgen Römisch, Marburg, both of (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/336,675

(22) Filed: Jun. 21, 1999

(30) Foreign Application Priority Data

Jun. 22, 1998 (DE) ........................................ 198 27 750

(51) Int. Cl.[7] ................................................ C07K 14/81

(52) U.S. Cl. ...................... 435/238; 435/235.1; 435/236; 435/283.1; 435/286.5; 422/28; 422/30; 422/44

(58) Field of Search ................................ 435/235.1, 236, 435/238, 283.1, 286.5, 19; 422/28, 30, 44; 210/501

(56) References Cited

U.S. PATENT DOCUMENTS

| | | |
|---|---|---|
| 5,622,930 | 4/1997 | Eldering et al. . |
| 5,643,770 | 7/1997 | Mason et al. . |
| 5,696,236 | 12/1997 | Omar et al. . |
| 5,939,389 | 8/1999 | Eisele et al. . |

FOREIGN PATENT DOCUMENTS

| | | |
|---|---|---|
| 4227762 A1 | 3/1994 | (DE) . |
| 0679436 | 11/1995 | (EP) . |
| WO 92/22320 | 12/1992 | (WO) . |
| WO 97/07674 | 3/1997 | (WO) . |

OTHER PUBLICATIONS

Gerencer et al. "Acquired Deficiency of Functional C1–Esterase Inhibitor in HIV Type 1–Infected Patients" *AIDS Research and Human Retroviruses*, vol. 13, No. 10(Jul. 1, 1997) pp. 813–4. RC607.A26.A35.*

* cited by examiner

*Primary Examiner*—Jeffrey Stucker
(74) *Attorney, Agent, or Firm*—Finnegan, Henderson, Farabow, Garrett and Dunner, L.L.P.

(57) ABSTRACT

A process for separating HIV from a fluid is described, in which the HIV is bound to a C1 esterase inhibitor immobilized on a support material. The process can be carried out both for the preparation of HIV-free blood donations and therapeutically for the reduction of the virus load in the blood by means of a blood lavage under the conditions of an extracorporeal blood circulation. The C1 esterase inhibitor can be bonded to a support material which is customary in affinity chromatography or to the fibers of a filter.

7 Claims, No Drawings

PROCESS FOR SEPARATING HIV FROM A FLUID

The invention relates to a process for separating human immunodeficiency virus or viruses (HIV) from a fluid, in particular from blood, blood plasma or blood serum. The process can be carried out both for the preparation of HIV-free blood donations and therapeutically for the reduction of the virus load in the blood by means of a blood lavage under the conditions of an extracorporeal blood circulation.

The invention is moreover directed at a filter which is suitable for the separation of HIV from a fluid.

It is known that the removal of HIV from all sorts of biological fluids, but especially from blood, blood plasma or blood serum, is an important prerequisite for its risk-free use for all sorts of medical purposes. Numerous processes have therefore already been proposed using which removal of HIV from biological fluids should be achieved. Thus, in the international Patent Application WO 97/07674, a process has been proposed using which HIV can be removed from biological fluids or inactivated by treating it with certain ethylenimine oligomers. It is important in this case that other constituents of the blood, in particular the cellular constituents, especially the erythrocytes, are not damaged by a treatment of this type and the removal of the HIV can be carried out in a simple manner and short period of time in order that sufficiently large amounts of purified blood can be obtained in an economically justifiable process.

It has now been found that these requirements can be fulfilled in an outstanding manner by a process if the C1 inhibitor is employed for the removal of the HIV from biological fluids.

The C1 inhibitor, also called C1 esterase inhibitor, is a protein which is present in the blood and is the main inhibitor of the classical pathway of the complement system and of the contact system. The C1 inhibitor can inhibit the activated form of factor XII and of kallikrein (Schapira M. et al., 1985, *Complement* 2: 111; Davis A. E., 1988, *Ann Rev Immunol* 6: 595; Sim R. B. et al., 1979, *FEBS Left* 97: 111; De Agostini A. et al., 1984, *J Clin Invest* 73: 1542; Pixley R. A. et al., 1985, *J Biol Chem* 206: 1723; Schapira M. et al., 1982, *J Clin Invest* 69: 462; Van der Graaf F. et al., 1983 *J Clin Invest* 71: 149; Harpel P. C. et al., 1975, *J Clin Invest* 55: 593). The C1 inhibitor thus regulates the activities of two plasma cascades, namely the complement system and the contact system, by which biologically active peptides are produced. The C1 inhibitor is therefore also an important regulator of the inflammatory system. Moreover, the C1 inhibitor inhibits activated factor XI (Meijers J. C. M. et al., 1988, *Biochemistry* 27: 959; Wuillemin W. A. et al., 1995, *Blood* 85: 1517). It follows from this that the C1 inhibitor can be considered as a coagulation inhibitor. The tissue plasminogen activator and plasmin are also inhibited to a certain extent by the C1 inhibitor, although that is not its main function (Harpel P. C. et al., 1975, *J Clin Invest* 55: 149; Booth N. A. et al., 1987 *Blood* 69: 1600).

The C1 inhibitor is obtained from plasma by purification to a considerable extent and utilized for clinical applications, in particular in the treatment of hereditary angioedema, a disorder which is caused by a genetically related deficiency of the C1 inhibitor. Moreover, it has already been described that good therapeutic results were achieved by administration of the C1 inhibitor in systemic inflammations

[International Patent Application WO 92/22320 (Genentech Inc.)], in severe burns, pancreatitis, bone marrow transplants, cytokine therapy and during use in extracorporeal blood circulations [DE-A4 227 762 (Behringwerke AG)].

The complete genomic and the cDNA which codes for the C1 inhibitor has already been cloned (Bock S. C. et al., 1986 *Biochemistry* 25: 4292; Carter P. E. et al., 1988, *Eur J Biochem* 173: 163). Various variants of the recombinant C1 inhibitor with amino acid mutations in the P1 and the P3 and/or P5 positions of the reactive center and variants which were isolated from patients with a hereditary angioedema have already been prepared recombinantly (Eldering E. et al., 1988, *J Biol Chem* 263: 11776; Eldering E. et al., 1993, *J Biol Chem* 267: 7013; Eldering E. et al., 1993, *J Clin Invest* 91: 1035; U.S. Pat. No. 5,622,930; Davis A. E. et al., 1992, *Nature Genetics* 1: 354; Eldering E. et al., 1995, *J Biol Chem* 270: 2579; Verpy et al., 1995, *J Clin Invest* 95: 350).

The C1 inhibitor belongs to the large family of serine proteinase inhibitors which are also called serpines (Travis J. et al., 1983, *Ann Rev Biochem* 52: 655; Carrel R. W. et al., 1985, *Trends Bioch Sci* 10: 20). On SDS-polyacrylamide gels, the C1 inhibitor exhibits a molecular weight of approximately 105 kD. Its plasma concentration is approximately 270 mg/l (Schapira M. et al., 1985, *Complement* 2: 111; Nuijens J. H. et al., 1989, *J Clin Invest* 84: 443). The C1 inhibitor is a protein whose plasma level can increase up to twofold in uncomplicated infections and other inflammations (Kalter E. S. et al., 1985, *J Infect Dis* 151: 1019). The increased formation of the C1 inhibitor in inflammations probably serves for the protection of the body against the harmful effects of the intravascular activation of the complement system and of the contact system during the acute reactions.

The serpines react as inhibitors by formation of bimolecular complexes with the proteinase to be inhibited. In these complexes, the active center of the proteinase is bound by the active center of the serpine and thus inactive (Travis J. et al., 1983, *Ann Rev Biochem* 52: 655). The serpines react specifically with certain proteinases, this specificity being determined by the amino acid sequence of the reactive center.

The abovementioned varied actions of the C1 inhibitor did not, however, give any indication of its strong affinity for HIV and in particular did not suggest that separation of HIV from biological fluids such as blood, blood plasma or blood serum is possible with the aid of the C1 inhibitor. It was therefore a very unexpected finding that HIV binds to the C1 inhibitor and can thereby be separated from mixtures which contain HIV with the aid of the processes below.

The invention relates to a process for separating HIV from a fluid such as blood, blood plasma or blood serum, in which the HIV is bound to a C1 esterase inhibitor immobilized on a support material. This process is expediently carried out such that the C1 esterase inhibitor is bonded to an inert matrix which can be employed in affinity chromatography, by means of which the biological fluid to be freed of the HIV is added in a procedure customary in column chromatography.

Suitable matrices on which the C1 inhibitor is immobilized include dextrans, polyacrylamides and agarose, but other supports customarily employed in affinity chromatography can also be used for the process according to the invention. As a result, HIV-free blood donations can be obtained. However, the virus load in the blood can also be therapeutically reduced if HIV is absorbed on a matrix impregnated with a C1 inhibitor by means of an extracorporeal blood lavage before or during chemotherapy.

A particularly effective and rapid separation of the HIV can be achieved according to the invention if the fluid containing the HIV is filtered through a fiber material which is impregnated with the C1 esterase inhibitor. For this, a filter has proven suitable which consists of a container in which is packed a fiber material which is impregnated with the C1 esterase inhibitor. The fiber material can either consist of fibers which are interwoven or entangled with one another or can be present in the form of a woven or web-like material. A particularly effective and rapid filtration can in this case be achieved using a filter which consists of fibers impregnated with the C1 esterase inhibitor which have an average diameter of less than 10 mm, preferably of 0.3 to 3 mm, and a bulk density of 0.15 to 0.5 g/cm$^3$ and an average fiber spacing of 0.5 to 0.7 mm.

Filters of this type are disclosed in European Patent Specification 0 155 003 and have proven so outstandingly suitable for filtering leukocytes from blood that they have largely been accepted in practice. However, no impregnated fibers and only fibers not actually impregnated with the C1 inhibitor are mentioned there. If, however, fibers impregnated with C1 inhibitor are employed in a filter system of this type, the affinity of this inhibitor for HIV can be combined with the advantages of rapid and effective filtration such that a biological fluid free of HIV can be obtained as a filtrate in a very simple manner.

The advantages of the process according to the invention are emphasized by the following example:

EXAMPLE

The following starting materials were employed:

HIV from cell cultures in RPMI medium (titer approximately $10^4$ $CCID_{50}$) C1 inhibitor-Sepharose: 5 mg of Ag/ml of Sepharose in 2 M NaCl, 20 mM tris pH 7.2

AT III-Sepharose: 11.1 mg of Ag/ml of Sepharose in 2 M NaCl, 20 mM tris pH 7.2

Experimental Procedure

HIV was pipetted 1:5 into the gel suspension (5 ml to 20 ml of gel suspension), the mixture was incubated at 22° C. for 30 min, the gel was centrifuged off at a low speed of rotation and the supernatant was titrated. The control employed was AT III-coupled Sepharose.

The following results were obtained:

| | Sepharose | | AT III-Sepharose | |
|---|---|---|---|---|
| Sample: HIV dilution | $CCID_{50}$* (determined) | $CCID_{50}$* (theoretical) | $CCID_{50}$* (determined) | $CCID_{50}$* (theoretical) |
| 1:1000 | ≦1.8 | 3.3 | 2.9 | 3.3 |

*$CCID_{50}log_{10}$ (cell culture infective dose 50%)

The experiment shows that HIV binds to C1-INH; the control experiment with AT III-coupled gel shows that the binding takes place specifically to C1-INH and not nonspecifically to gel.

The experiment was carried out using approximately 50,000 infectious virions of HIV in the experimental batch; at least approximately 48,000 virions were removed from the supernatant by 100 mg of gel-bound C1 inhibitor.

What is claimed is:

1. A process for separating HIV from a fluid, which comprises binding the HIV to a C1 esterase inhibitor immobilized on a support material.

2. The process as claimed in claim 1, wherein the fluid employed is blood, blood plasma or blood serum.

3. The process as claimed in claim 1, wherein the support material used is an inert matrix which can be employed in affinity chromatography.

4. The process as claimed in claim 1, wherein the HIV-containing fluid is filtered through a fiber material which is impregnated with the C1 esterase inhibitor.

5. A filter for separating HIV from a fluid, which consists of a container in which is packed a fiber material which is impregnated with the C1 esterase inhibitor.

6. The filter as claimed in claim 5, wherein the fiber material consists of fibers which are interwoven or entangled with one another or is present in the form of a woven or web-like material.

7. The filter as claimed in claim 5, wherein the fibers impregnated with the C1 esterase inhibitor have an average diameter of less than 10 mm, preferably of 0.3 to 3 mm, a bulk density of 0.15 to 0.5 g/cm$^3$ and an average fiber spacing of 0.5 to 0.7 mm.

* * * * *